United States Patent [19]

Anderson

[11] Patent Number: 5,113,023
[45] Date of Patent: May 12, 1992

[54] REMOVAL OF LINEAR INTERNAL OLEFINS FROM STEAM ACTIVE DEHYDROGENATION RECYCLE STREAM

[75] Inventor: Richard L. Anderson, Bartlesville, Okla.

[73] Assignee: Phillips Petroleum Company, Bartlesville, Okla.

[21] Appl. No.: 552,868

[22] Filed: Jul. 16, 1990

[51] Int. Cl.$^5$ .............................................. C07C 41/06
[52] U.S. Cl. .................................. 568/697; 585/259; 585/324; 585/670
[58] Field of Search ................ 568/697; 585/259, 324, 585/670

[56] References Cited

U.S. PATENT DOCUMENTS

| | | | |
|---|---|---|---|
| 2,428,516 | 10/1947 | Drennan | 260/677 |
| 3,485,887 | 12/1969 | Kronig et al. | 260/677 |
| 3,979,461 | 9/1976 | Ancillotti et al. | 260/614 |
| 4,118,425 | 10/1978 | Herbstman | 260/614 A |
| 4,581,474 | 4/1986 | Hutson, Jr. et al. | 568/697 |

Primary Examiner—Howard T. Mars
Assistant Examiner—Kimberly J. Kestler
Attorney, Agent, or Firm—Laney, Dougherty, Hessin & Beavers

[57] ABSTRACT

A process in which isobutane (isoparaffins), containing normal butane (normal paraffins), is dehydrogenated, and the principal product, isobutene, (isoolefin) contains some butene-1 and butene-2 (1-olefins and linear internal olefins). This mixture is subjected to a catalyzed etherification reaction with an alcohol to yield tertiary-alkyl ether. Some unreacted butene-1 and butene-2 (linear olefins) appear in the effluent from the ether reacton zone. These detrimentally affect the advantage of recycling that part of the effluent constituted by isobutane (isoparaffin) to the dehydrogenation reactor, because, as they build up in the closed system, undesirable coke lay down on the dehydrogenating catalyst occurs. The undesirable butene-1 is hydroisomerized to butene-2 which is removed from the recycle stream by fractionation.

16 Claims, 1 Drawing Sheet

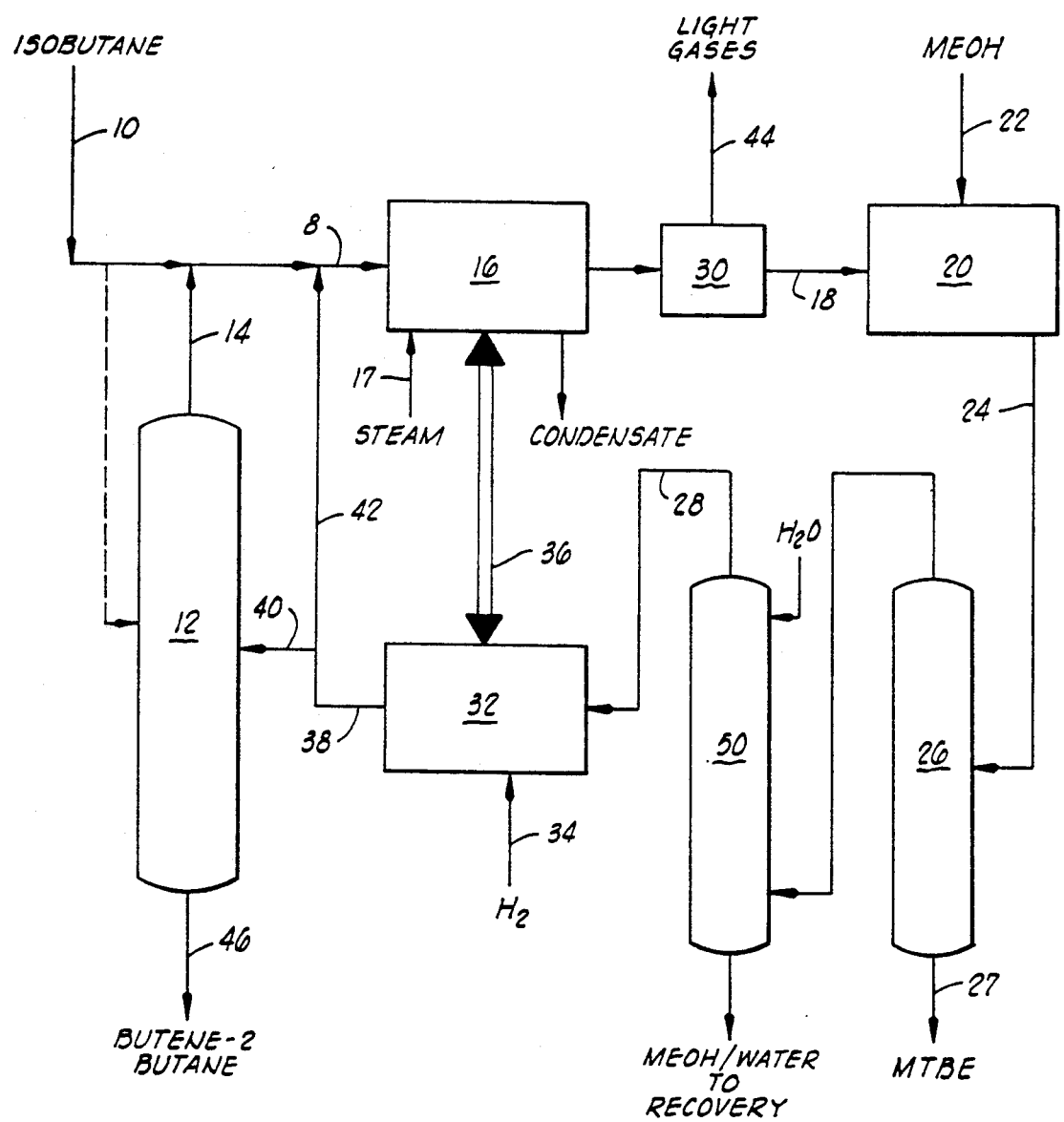

REMOVAL OF LINEAR INTERNAL OLEFINS FROM STEAM ACTIVE DEHYDROGENATION RECYCLE STREAM

FIELD OF THE INVENTION

This invention relates to production of tertiaryalkyl ethers from isoparaffin hydrocarbons, and more particularly, to a process in which the isoparaffins are initially dehydrogenated to isoolefin compounds then charged to an etherification reaction. Unreacted linear $\alpha$-olefins in the etherification reactor effluent are converted to relatively higher boiling internal olefins, which are removed from a recycle stream to the dehydrogenation reactor.

BACKGROUND OF THE INVENTION

BRIEF DESCRIPTION OF THE PRIOR ART

Tertiaryalkyl ethers are compounds desirably used in the blending of high octane premium unleaded gasolines. It is known to produce such ether compounds in an etherification reactor in which a lower, water soluble alkanol, such as methanol, is reacted with an isoolefinic compound derived from an isoparaffin to yield the tertiaryalkyl ether. The isoolefin compound is produced by charging an isoparaffin of the desired number of carbon atoms to a dehydrogenation zone in which the isoparaffin is dehydrogenated to the corresponding iso-olefin over a suitable dehydrogenation catalyst. A process by which ethers are prepared in the manner described is disclosed in U.S. Pat. No. 4,118,425. In the described etherification process, it is useful to recycle to the dehydrogenation reactor unreacted isoparaffins which have not been dehydrogenated in the dehydrogenation zone, and therefore not reacted in the etherification zone.

The advantage achieved by recycling isoparaffin compounds to the dehydrogenation reactor is impaired by the inclusion in the effluent from the etherification reactor of linear olefinic materials. These olefinic materials, such as, for example, butene-1, butene-2 and butadiene, pass through the etherification reactor intact after having been formed in small quantities in the dehydrogenation of the isoparaffin compounds to the corresponding isoolefins. Since the linear olefin compounds pass through the entire closed system without undergoing significant reaction, except for some conversion of the monounsaturated butenes to butadiene, they tend to build up as the cyclic process is continued. This build up will ultimately result in the lay down of coke on the dehydrogenation catalyst bed, thereby shortening the effective life of the catalyst prior to the time when it would otherwise require regeneration.

Some linear paraffins will usually be present in the isoparaffin charge to the dehydrogenation catalyst, and, while being partially converted to the normal olefin compounds described, will also, in part, continue through the dehydrogenation and etherification reactions in small quantities of the unchanged normal paraffins. Such compounds are also unaffected by the etherification reaction, and it is desirable to remove them from the recycle stream which is passed from the etherification reaction zone to the dehydrogenation reactor.

In U.S. Pat. No. 4,581,474, a stream which comprises a mixture of butene-1, butene-2 and isobutene is charged to a conventional methyltertiarybutyl ether (MTBE) plant, along with methanol. In the etherification reactor, the isobutene reacts with the methanol to yield MTBE. After recovery of the MTBE, the effluent stream, now enriched in linear butenes, is passed to an adsorption zone where a large portion of the butene-2 content of the stream is adsorbed. In this adsorption zone, a molecular sieve is utilized to relatively adsorb butene-2 from butene-1. The effluent from the adsorption unit is a butene-1 rich stream, and this is divided into two streams. One of these is subjected to a double bond isomerization to convert the butene-1 to butene-2. The butene-1 in the other of the two streams is isomerized to isobutene which is then recycled to the MTBE reactor to supplement the fresh isobutene charge stock. This patent is not concerned with the preparation of the initial or original isobutene charge stock to the MTBE reactor, and thus does not disclose the preparation of this material by dehydrogenation of the corresponding isobutane. Neither is this patent concerned, therefore, with the recycling of an isoparaffin recycle stream to a dehydrogenation reactor, or the removal of undesirable linear olefin compounds therefrom.

BRIEF DESCRIPTION OF THE PRESENT INVENTION

By the present invention, the process efficiency, and more particularly, the catalyst longevity, of a process by which tertiary alkyl ethers are produced is substantially improved. The improvement involves the continuous removal of certain linear olefinic by-products which are detrimental to this procedure, which procedure entails initially dehydrogenating isoparaffin hydrocarbons to isoolefinic compounds followed by alcoholysis of the isoolefins to yield tertiary alkyl ethers. By reason of such removal of undesirable linear olefins the process is not hindered by the build up of these undesirable compounds in the streams continuously recycled between the etherification zone and the dehydrogenation reactor. The principal removed compounds constitute valuable by-products which can be used for a variety of purposes, such as, for example, the manufacture of butadiene or other useful compounds.

Broadly described, the process of the invention initially charges an isoparaffin stream, which also contains small amounts of normal paraffins, plus some linear olefinic materials, to a dehydrogenation reactor where the isoparaffins are dehydrogenated to isoolefinic compounds. This dehydrogenation reaction has been carried out with several catalysts and varying process conditions. In one embodiment, a bed of a steam active dehydrogenation catalyst is used for dehydrogenating the isoparaffins to yield the corresponding isoolefins. This catalyst is periodically regenerated. A procedure in which the steam active dehydrogenation catalyst is used for this purpose is described in U.S. Pat. No. 4,229,609 which is incorporated herein by reference.

After isoolefin is produced by the described dehydrogenation reaction, it is charged to a catalyzed etherification reaction zone where it is reacted with a lower alcohol ($C_1$–$C_5$) to yield a tertiary alkyl ether. Some of these ethers constitute valuable additives to high octane gasoline. The ether thus produced is to some extent an impure product, and the effluent from the etherification reaction, while containing some isoparaffin which can be advantageously recycled to the dehydrogenation reaction zone, also includes certain linear paraffinic and linear olefinic compounds. By reason of their propensity to build up during the recycling conducted in the process, they undesirably affect the performance of the dehydrogenation catalyst by shortening its effective service life in the process prior to the need for the regeneration of such catalyst.

Furthermore, reactor capacity is not efficiently utilized by the buildup of linear paraffins and olefinic compounds, since they cannot produce the desired tertiary alkyl ether.

The present invention proposes to convert linear 1-olefins present in the etherification reactor effluent to higher boiling internal olefinic isomers which can then be removed by fractionation from the stream recycled to the dehydrogenation reactor.

It is one object of the present invention to improve the efficiency and service life of a catalytic dehydrogenation unit when used in conjunction with a catalytic etherification reactor to convert the products yielded by the dehydrogenation unit to valuable ether compounds.

Another object of the invention is to effectively remove present amounts of dehydrogenation catalyst-poisoning butadiene from an isobutane stream undergoing recycling to a dehydrogenation reaction zone.

A further object of the invention is to provide an integrated process for the production of tertiary alkyl ethers, which process can operate longer and more effectively before requiring regeneration of a certain catalyst used in the process.

Another object of the invention is to minimize the lay down of coke on a steam active dehydrogenation catalyst during the time when such catalyst is in continuous use in a procedure in which the charge stock to the dehydrogenation zone is a mixture of fresh paraffinic charge material and a recycle stream which includes isoparaffins, normal paraffins and linear olefins recycled from a downstream etherification process which is used conjunctively with the dehydrogenation reaction.

Additional objects and advantages of the invention will become apparent as the following detailed description of the invention is read in conjunction with the accompany drawing which is a process flow diagram schematically illustrating the process of the invention, and showing certain dehydrogenation and etherification reactor units employed therein.

In accordance with one embodiment of this invention, the process is improved by the inclusion therein of an isomerization reaction in which linear 1-olefins are converted to internal olefins in a recycle stream in which the build up of linear olefins is undesirable. The internal olefins have a relatively higher boiling point than the other components of the recycled stream from which it is desired to separate linear olefins, and to prevent their build up as the continuous process is operated.

A further object of the invention is to facilitate the removal of internal olefins and normal paraffins from a process stream where their build up in a recycle stream is detrimental. The conversion of the 1-olefin in the recycled stream to the internal 2-olefin of higher boiling point allows the latter to be readily removed by fractionation from isoparaffin and isoolefin materials of the same number of carbon atoms.

GENERAL DESCRIPTION OF THE DRAWING

The drawing is a schematic illustration of one embodiment of the process of the invention. For purposes of simplicity and ease of understanding, many pieces of apparatus which are required for the successful operation of the process, such as pumps, compressors, temperature and pressure flow rate monitoring and control systems, flow control valves, etc., have not been shown. This schematic representation of one embodiment of the invention is not intended to exclude from the scope of the inventive concept, those other embodiments which are not expressly disclosed herein, but which result from reasonable and anticipated modifications which may be made by those skilled in the art, or are clear and readily apparent equivalents of the process units, and methodology steps.

DETAILED DESCRIPTION OF A PREFERRED EMBODIMENT OF THE INVENTION

As illustrated in the drawing, a process feed stream which includes primarily isobutane, but which also includes some n-butane, is fed through a process flow line or conduit 10 and is combined with overhead 14 from a fractionator 12, such as a conventional multitray tower. Alternatively, as shown by the dashed line, some or all of the feed could be sent directly to the fractionator 12. In the fractionator 12, a portion of the recycled mixture of $C_4$ hydrocarbons hereinafter described, is subjected to fractionation so that the relatively low boiling materials, including primarily isobutane with some butene-1 and some isobutylene, pass overhead and are charged via a conduit 8 to a catalytic dehydrogenation reactor 16. The bottoms or kettle products from the fractionator 12 include principally normal butane and butene-2.

The dehydrogenation reactor 16 is of conventional construction, and may use various catalysts known in the art. The dehydrogenation reactor is preferably a steam active dehydrogenation reactor and preferably employs a catalyst which is broadly a Group VIII metal on a support. The preferred Group VIII metal is platinum. The support can be alumina, silica, magnesia, zirconia, alumina-silicates, Group II metal aluminate spinels, and mixtures of such supports. Group II metals and Group VIII metals are those classified in Group II and Group VIII of the Periodic Table of the Elements as set forth in Chemical Rubber Company, "*Handbook of Chemistry and Physics*", 45th Edition (1964), p. B-2.

The amount of the Group VIII metal used is not critical. Generally any amount resulting in catalytic activity of the support/metal combination when made active with steam can be utilized. Typically, the Group VIII metal is present in the catalyst in an amount in the range of from about 0.01 to about 10 parts by weight, per 100 parts by weight of the support, and most frequently the quantity is in the range of about 0.1 to about 5 parts by weight.

Co-promotor metals can be employed in the catalyst in conjunction with the Group VIII metal. The preferred copromotors are lead, tin and germanium. The co-promotor, when employed, will typically be used in the range of from about 0.01 to 10 parts by weight and frequently in a range of from about 0.1 to 5 parts by weight of co-promotor per 100 parts by weight of support. The co-promotor metals can be employed as chemical compounds, such as halides, nitrates, oxylates, acetates, carbonates, propionates, tartrates, chromates, chlorates, oxides and hydroxides, etc. Among the co-promotors, tin is the preferred metal and conveniently and effectively stannous halides can be utilized.

The catalysts used in the dehydrogenation carried out in the reactor 16, when using the Group VIII metal preferred species hereinbefore described, are obtained by impregnating the support for the Group VIII metal compound and copromotor metals, if any, using known methods. The metal compounds employed should be such that upon calcination of the catalyst, no significant amount of extraneous material remains on the catalyst, particularly no additional metals which would interfere with the activity of the catalyst in the dehydrogenation reaction.

The preferred dehydrogenation catalyst useful in the processes of this invention is a catalyst comprising platinum on zinc aluminate, particularly and preferably zinc aluminate spinel. Most preferably, the catalyst is co-promoted with tin. The most preferred catalyst of the invention is therefore essentially zinc aluminate spinel, platinum and tin. Typically, the catalyst can contain from about 0.1 to about 5 parts by weight of platinum, and from about 0.1 to about 1 part by weight of tin on 100 parts by weight of a zinc aluminate spinel support. The preferred catalyst has a pore volume in the range of 0.23–0.55 cc/g, and a surface area in the range of from about 12 to about 30 m$^2$/g.

Steam is introduced into the dehydrogenation reactor via the line 17 while typically maintaining the reactor at a temperature of from about 950° F. to about 1150° F., and a pressure of from about 20 psig to about 100 psig.

In the dehydrogenation reactor 16, the charge stock to the reactor is chemically converted so that effluent from the reactor consists of isobutylene and unreacted isobutane, some butene-1, some butene-2, a small amount of normal butane and a very small amount of butadiene. This mixture, after removal of light gases in the unit 30 via the overhead conduit 44, typically includes various branched and linear, as well as saturated and unsaturated, C$_4$ hydrocarbons. This stream is charged through conduit 18 to an etherification reactor 20. In the etherification reactor, methyltertiarybutyl ether is produced from the reaction of the isobutylene with methyl alcohol charged to the reactor via a conduit 22. In the generic statement of the invention, the iso-olefin in the mixture charged to the etherification reactor, or ether forming zone, is reacted with a water soluble lower alkanol to form a particular ether product which is desired.

The ether forming reaction which occurs in the etherification reactor 20 is well known. The catalyst employed is a conventional ether forming catalyst, and such have been described in U.S. Pat. Nos. 3,979,461 and 3,902,870. Specific examples of such catalysts are aluminum chloride (AlCl$_3$), hydrogen fluoride and sulfuric acid, as well as acetic ion exchange resins.

Typical ether forming conditions which prevail in the etherification reaction zone 20 are given in following Table I.

TABLE I

| Etherification Reaction Conditions | | |
|---|---|---|
| | Generally Employed | Preferably Employed |
| Temperature (°F.) | 90–200 | 100–170 |
| Pressure (psig) | 40–600 | 85–260* |
| LHSV** | 0.2–30 | 0.5–20 |
| Isoolefin/Alcohol (mole ratio) | 0.2–2 | 0.8–1.3 |

*Pressure is sufficient to maintain the reactants in the liquid phase.
**Liquid Hourly Space Velocity; volume of hydrocarbon per volume of catalyst per hour.

Typical alcohols used in the ether forming reaction are alkanols having from one to three carbon atoms. Methanol, in view of its availability, is presently the preferred alcohol for use in the etherification reaction.

The effluent from the etherification reactor 20 is passed via the conduit 24 to a fractionation tower 26 where the relatively high boiling tertiary alkyl ether, such as methyltertiarybutyl ether, is removed as the bottoms or kettle product via the conduit 27, and unreacted isobutane, isobutylene, n-butane, butene-1, butene-2, methanol and a small amount of butadiene pass from the fractionator as overhead. Methanol is removed from the C$_4$'s by extraction with water in vessel 50, and the C$_4$ raffinate stream enters line 28. The principal component of the overhead stream in line 28 is isobutane, but the stream also contains amounts of n-butane, butene-1 and butene-2 which are significant in terms of compounds which will build up in the recycling, continuously operated process of the present invention, and will detrimentally affect the catalyst and reactor efficiency in the dehydrogenation reactor as a result of such buildup. A small amount of butadiene is also present in the overhead. The overhead containing the named C$_4$ compounds is passed via the line 28 to a hydroisomerization reactor 32.

The hydroisomerization reaction occurring in the hydroisomerization reaction zone 32 is a liquid phase reaction and there is therefore no need to vaporize the C$_4$ mixture which is charged thereto. The reaction is carried out under hydrogen charged to the reaction zone 32 via a line 34.

The catalyst which is used in the hydroisomerization reactor 32 is preferably a palladium-on-alumina catalyst. The catalyst will typically contain from about 0.3 weight percent to about 0.5 weight percent palladium. Other catalytic materials effective to bring about the isomerization of butene-1 to butene-2 can also be used.

The hydroisomerization reaction occurring in the reactor 32 is, as indicated, preferably carried out in the liquid phase. The pressure is therefore maintained in the reactor at a magnitude which is at least sufficient to maintain the reactants and catalyst diluent in the liquid phase. The pressure in the reactor can range from about 250 psig to about 500 psig, observing the minimum pressure required to maintain the liquid phase reaction condition described. Typically, the pressure in the hydroisomerization reactor is about 400 psig.

The temperature in the hydroisomerization reactor 32 is generally between about 150° F. and about 250° F., and preferably is from about 150° F. to about 200° F. Typically, the temperature is about 180° F. The reactor 32 can be operated over a range of temperature, pressure and space velocity conditions, and will be operated over a range of conditions as the catalyst activity varies with aging and due to other conditions. The Liquid Hourly Space Velocity (LHSV) is usually from about 8 to about 11, with a LHSV of about 10 being preferred.

The hydrogen charged to the reactor 32 is charged in an amount which is generally based on the concentration of the butadiene in the mixture of C$_4$ hydrocarbons charged to the reactor. Preferably, the mole ratio of hydrogen to butadiene which determines the charge of hydrogen is about 2:1. The hydrogen to butadiene ratio can also be changed in response to variation in the catalyst activity.

In general, the reaction conditions of temperature, pressure, hydrogen to butadiene charge ratio and LHSV will be changed to maintain the effectiveness of the hydroisomerization reactor in isomerizing the linear butene-1 compounds to butene-2. Such isomerization and the removal of butadiene are the primary objects of the use of the hydroisomerization reactor in the process of the invention.

In the hydroisomerization reactor 32, generally at least ninety-five percent of the butadiene is converted to a mixture of products including various mono-unsaturated $C_4$ olefins and some n-butane. Moreover, recycle to the dehydrogenation reactor 16 after merging with the fresh isobutane make-up from stream 10 and the overhead from fractionation column 12.

In Table II, typical component flow rates in the various process flow streams are shown in weight units/unit of time.

TABLE II

| Component | Stream 10 | Stream 14 | Stream 40 | Stream 46 | Stream 38 | Stream 8 | Stream 44 | Stream 18 | Stream 22 | Stream 27 | Stream 28 | Stream 34 |
|---|---|---|---|---|---|---|---|---|---|---|---|---|
| Hydrogen | | | | | | | 3.77 | | | | | 0.01 |
| $CO_2$/CO | | | | | | | 4.66 | | | | | |
| Methane | | | | | | | 0.86 | | | | | |
| $C_2/C_2=$ | | | | | | | 0.14 | | | | | |
| $C_3/C_3=$ | 2.70 | | | | | 2.70 | 4.01 | | | | | |
| Isobutane | 95.75 | 24.89 | 24.89 | 0.00 | 99.56 | 195.31 | | 99.56 | | | 99.56 | |
| Isobutylene | | 0.92 | 0.92 | 0.00 | 3.68 | 3.68 | | 91.89 | | | 3.68 | |
| 1-Butene | | 0.13 | 0.13 | 0.00 | 0.52 | 0.52 | | 1.13 | | | 1.13 | |
| Butadiene | | 0.00 | 0.00 | 0.00 | 0.00 | 0.00 | | 0.08 | | | 0.08 | |
| n-Butane | 1.55 | 0.06 | 1.21 | 1.15 | 4.84 | 5.24 | | 4.76 | | | 4.76 | |
| t-2-Butene | | 0.02 | 0.45 | 0.43 | 1.79 | 1.36 | | 1.43 | | | 1.43 | |
| c-2-Butene | | 0.00 | 0.33 | 0.33 | 1.31 | 0.99 | | 1.05 | | | 1.05 | |
| C5+ | | 0.00 | | | | | | 0.10 | | 0.10 | | |
| MeOH | | | | | | | | | 52.51 | | | |
| MTBE | | | | | | | | | | 138.62 | | |
| TOTAL | 100.00 | 26.02 | 27.93 | 1.91 | 111.70 | 209.80 | 13.44 | 200.00 | 52.51 | 138.72 | 111.69 | 0.01 | and importantly, the mole ratio of butene-2 to butene-1 in the effluent from the hydroisomerization reactor is about 6:1, compared with a mole ratio of 2:1 in the feed to the reactor. Thus, it will be perceived that there is a very significant conversion of butene-1 to butene-2 in the hydroisomerization reactor.

In addition to isomerization of a major portion of the butene-1 to butene-2, the hydrogen charge to the hydroisomerization reactor also effectively converts some of the linear butene compounds to saturated $C_4$ compounds, particularly n-butane. This, too, is a desirable reaction because the n-butane can be more easily removed from the recycled stream than can butene-1 as a result of the relatively higher boiling point of the n-butane.

It should be pointed out that in typically heating the hydroisomerization reactor to about 180° F. and in keeping the contents of the reactor in the liquid phase, it is possible, and is of advantage, to include a heat exchange loop coupling the hydroisomerization reactor 32 with the steam active dehydrogenation reactor 16. Such a loop is shown in the drawing, and is there denominated by reference numeral 36. The steam used in the steam active dehydrogenation reactor must be subsequently cooled in order to condense the steam, and the heat exchange fluid is thereby heated to an elevated temperature useful in attaining and maintaining the desired temperature within the hydroisomerization reactor 32.

From the hydroisomerization reactor 32, the effluent flows through a conduit 38 to a point where a purge stream is removed from the principal stream through a conduit 40 and passed to the fractionation column 12. Typically, about 25 weight percent of the flow in the conduit 38 is purged to the fractionator 12. In the fractionator 12, the relatively heavy (high boiling) butene-2 component of the purge stream is removed, along with normal butane, as a bottoms fraction via the conduit 46. The isobutane constituting a major component in the stream 38 passes as overhead from the fractionation tower 12, and is joined with the isobutane from the feed line 10.

The principal stream remaining after the purge stream is split therefrom moves through a conduit 42 for Reasonable variations and modifications which will become apparent to those skilled in the art can be made from this invention without departing from the spirit and scope thereof.

What is claimed is:

1. In a process for dehydrogenating a stream which comprises a major amount of isobutane and a minor amount of n-butane to yield an effluent which consist essentially of isobutylene, unreacted isobutane, butene-1, butene-2, n-butane and butadiene, then reacting the effluent product of the dehydrogenation with a $C_1$–$C_3$ lower alkanol to consume isobutylene and yield as an effluent, a mixture which comprises unreacted isobutane, butene-1, butene-2, butadiene and an alkyltertiarybutyl ether, the improvement which comprises:

separating the alkyltertiarybutyl ether from the reminder of the last-mentioned effluent mixture;

hydroisomerizing said remainder of the last-mentioned effluent mixture to convert butadiene therein to linear mono-unsaturated butenes and n-butane, and to isomerize the butene-1 in said remainder of the last-mentioned effluent mixture to butene-2 and n-butane; then fractionating the hydroisomerized remainder of the last-mentioned effluent mixture to separate butene-2 and n-butane from relatively lower boiling components, including isobutane, in an overhead stream; and recycling at least a major portion of the separated overhead stream, including isobutane, to dehydrogenation.

2. The improvement defined in claim 1 wherein the hydroisomerization of said remainder of the last-mentioned effluent mixture resulting in the isomerization of the butene-1 and hydrogenation of butadiene is carried out by:

passing said remainder of the mixture over a hydroisomerization catalyst which comprises a palladium-on-alumina catalyst; and concurrently charging hydrogen to the hydroisomerization reaction zone containing the catalyst.

3. The improvement defined in claim 1 wherein the dehydrogenation is a steam active dehydrogenation process in which isobutane is contacted with a catalyst which is a Group VIII metal supported on a support selected from the group consisting of alumina, silica, magnesia, zirconia, alumina-silicates, Group II metal aluminate spinels and mixtures thereof; and concurrently passing steam into the dehydrogenation reactor while maintaining the reactor at a temperature of from about 950° F. to about 1150° F. and a pressure of from about 20 psig to about 100 psig.

4. The improvement defined in claim 3 wherein said Group VIII metal is platinum, and said support is a zinc aluminate spinel.

5. The improvement defined in claim 1, wherein said alkanol is methanol and the ether produced is methyltertiarybutyl ether.

6. The improvement defined in claim 5 wherein the methyltertiarybutyl ether produced in said etherification reaction is separated from the remainder of the mixture by fractionating the mixture to remove the relatively high boiling methyltertiarybutyl ether from the remainder of the mixture.

7. The improvement defined in claim 2 wherein the dehydrogenation is a steam active dehydrogenation process in which isobutane is contacted with a catalyst which is a Group VIII metal supported on a support selected from the group consisting of alumina, silica, magnesia, zirconia, alumina-silicates, Group II metal aluminate spinels and mixtures thereof; and concurrently passing steam into the dehydrogenation reactor while maintaining the reactor at a temperature of from about 950° F. to about 1150° F. and a pressure of from about 20 psig to about 100 psig.

8. A process for producing alkyltertiarybutyl ether which comprises:

subjecting to a dehydrogenation reaction, a mixture comprising isobutane and n-butane to yield a reaction product effluent mixture which includes light gases, isobutane, butene-1, butene-2, butadiene, isobutylene and n-butane;

removing light gases from the reaction product mixture;

charging the remaining reaction product mixture to an etherification reactor, and there reacting at least a portion of the isobutylene with an alkanol containing from 1 to 3 carbon atoms to yield an alkyltertiarybutyl ether in a reaction product mixture form the etherification reactor, said reaction product mixture from the etherification reactor further including unreacted alkanol, isobutane, butene-1, butene-2, and butadiene;

separating the alkyltertiarybutyl ether from the remainder of the reaction product mixture from the etherification reactor;

separating unreacted alkanol from that portion of the reaction product mixture from the etherification reactor which remains after removal of the ether therefrom;

subjecting the etherification reactor reaction product mixture, following the removal of ether and alkanol therefrom, to a hydroisomerization reaction carried out in a hydroisomerization reactor to convert butene-1 to butene-2, and to concurrently hydrogenate butadiene to n-butane and linear mono-unsaturated butenes; then fractionating the hydroisomerized mixture to remove a major portion of the butene-2 and n-butane as an overhead therefrom; and recycling a major portion of the overhead from said fractionation to said dehydrogenation reaction.

9. The process as defined in claim 8 wherein said alkanol is methanol.

10. The process as defined in claim 8 wherein said dehydrogenation reaction is a steam active dehydrogenation process which includes the steps of:

contacting isobutane with a catalyst which is a Group VIII metal supported on a support selected from the group consisting of alumina, silica, magnesia, zirconia, alumina-silicate, Group II metal aluminate spinels and mixtures thereof; and concurrently passing steam into the dehydrogenation reactor while retaining the reactor at a temperature of from about 950° F. to about 1150° F. under pressure from about 20 psig to about 100 psig.

11. The process as defined in claim 10 wherein said Group VIII metal is platinum and said support is an aluminate spinel.

12. The process as defined in claim 8 wherein said hydroisomerization reaction is a liquid phase reaction carried out over a catalyst which comprises palladium-on-alumina, and the reaction is carried out at a pressure ranging from about 250 psig to about 500 psig, maintaining a minimum pressure as required to maintain the liquid phase reaction condition, and maintaining a temperature of between about 150° F. and about 250° F., and carrying out the reaction at a LHSV of from about 8 to about 11, all while concurrently charging hydrogen to the hydroisomerization reaction zone containing the catalyst.

13. The process as defined in claim 12 wherein said dehydrogenation reaction is a steam active dehydrogenation process which includes the steps of:

contacting isobutane with a catalyst which is a Group VIII metal supported on a support selected from the group consisting of alumina, silica, magnesia, zirconia, alumina-silicate, Group II metal aluminate spinels and mixtures thereof; and concurrently passing steam into the dehydrogenation reactor while retaining the reactor at a temperature of from about 950° F. to about 1150° F. under pressure from about 20 psig to about 100 psig.

14. The process as defined in claim 13 wherein said Group VIII metal is platinum and said support is an aluminate spinel.

15. The process as defined in claim 13 wherein said alkanol is methanol.

16. A process for preparing alkyltertiarylalkyl ether compounds by reacting isoolefinic compounds with a lower alkanol which comprises:

subjecting to a dehydrogenation reaction, a mixture of hydrocarbons containing isoparaffin and n-paraffin compounds to yield a reaction mixture which contains principally isoolefinic compounds and some 1-olefins and linear internal olefins;

subjecting said reaction mixture to a catalyzed etherification reaction with a lower alkanol to yield an alkyltertiaryalkyl ether, mixed with some linear monoolefinic compounds and di-olefinic compounds and some isoparaffin;

removing the ether from the mixture yielded by the etherification reactor;

subjecting the mixture following ether removal to a hydroisomerization reaction in which 1-olefin is converted to 2-olefin;

removing 2-olefin produced by the hydroisomerization reaction from the mixture to produce a recycle stream containing isoparaffin; then recycling the recycle stream containing isoparaffin to the dehydrogenation reaction.

* * * * *

UNITED STATES PATENT AND TRADEMARK OFFICE
CERTIFICATE OF CORRECTION

PATENT NO. : 5,113,023
DATED : May 12, 1992
INVENTOR(S) : Richard L. Anderson It is certified that error appears in the above-identified patent and that said Letters Patent is hereby corrected as shown below:

In Column 8, line 42, delete "minder" and insert --mainder--.
In Column 9, line 49, delete "form" and insert --from--.
In Column 9, line 68, after the word "n-butane" insert --therefrom--.
In Column 9, line 69, delete the word "therefrom".

Signed and Sealed this

Sixth Day of July, 1993

Attest:

MICHAEL K. KIRK

Attesting Officer

Acting Commissioner of Patents and Trademarks